United States Patent [19]

Hunter

[11] Patent Number: 5,152,979
[45] Date of Patent: Oct. 6, 1992

[54] METHOD FOR TREATING VASCULAR OBSTRUCTIONS CAUSED BY ABNORMAL CELLS

[75] Inventor: Robert L. Hunter, Tucker, Ga.

[73] Assignee: Emory University, Atlanta, Ga.

[21] Appl. No.: 745,066

[22] Filed: Aug. 14, 1991

Related U.S. Application Data

[60] Continuation-in-part of Ser. No. 522,297, May 11, 1990, Pat. No. 5,047,236, which is a continuation of Ser. No. 403,017, Sep. 5, 1989, abandoned, which is a continuation of Ser. No. 303,791, Jan. 30, 1989, abandoned, which is a division of Ser. No. 45,459, May 7, 1987, Pat. No. 4,801,452, which is a continuation-in-part of Ser. No. 43,888, Apr. 29, 1987, abandoned, which is a continuation of Ser. No. 863,582, May 15, 1986, abandoned.

[51] Int. Cl.$^5$ ......................................... A61A 31/745
[52] U.S. Cl. ............................... 424/78.38; 514/723
[58] Field of Search .......................... 424/83; 512/895

[56] References Cited

U.S. PATENT DOCUMENTS

| | | | |
|---|---|---|---|
| 2,674,619 | 4/1954 | Lunsted | 560/198 |
| 3,450,502 | 6/1960 | Hymes | 422/38 |
| 3,577,522 | 5/1971 | Hymes | 424/78 |
| 3,590,125 | 6/1971 | Hymes | 424/78 |
| 3,641,240 | 2/1972 | Hymes et al. | 424/78 |
| 3,956,259 | 5/1976 | Garcia et al. | 530/830 |
| 3,980,772 | 9/1976 | Ginger et al. | 424/94.64 |
| 4,073,886 | 2/1978 | Kehm | 530/833 |
| 4,186,253 | 1/1980 | Yokoyama et al. | 435/240 |
| 4,395,393 | 7/1983 | Schmolka | 424/78 |
| 4,600,652 | 7/1986 | Solomon et al. | 428/423.3 |
| 4,609,546 | 9/1986 | Hiratani | 424/83 |

FOREIGN PATENT DOCUMENTS

5094 1/1979 Japan.
1183112 10/1985 U.S.S.R..

OTHER PUBLICATIONS

Schmolka, I., "A Review of Block Polymer Surfactants", *Journal of the American Oil Chemists Society*, 54, No. 3, pp. 110–116 (1977).

Block and Graft Copolymerization, vol. 2, (ed. by R. J. Ceresa, John Wiley & Sons, 1976) "The Applications of Block Copolymer Polyol Surfactants"L. G. Lundsted and I. R. Schmolka; pp. 174–205 and pp. 255–272 (references).

Reindorf, C. A., et al., "Perfluorocarbon Compounds: Effects on the Rheological Properties of Sickle Erythrocytes in vitro", *American Journal of Hematology*, vol. 19, pp. 229–236, (1985).

Padilla, F., et al., "Effect of Fluorocarbon emulsions on the mechanical fragility of normal and sickle cells: in vitro studies" Federation Proceedings, vol. 34, pp. 1510–1512, (1975).

Vercellotti, G. M., et al., "Activation of Plasma Complement by Perfluorocarbon Artificial Blood: Probable Mechanism of Adverse Pulmonary Reactions in Treated Patients and Rationale for Corticosteroid Prophylaxis", *Blood*, vol. 59, pp. 1299–1304, (1982).

Janoff, A. S., et al., "The Modification of Human Erythrocyte Membrane Structure by Membrane Stabilizers: An Electron Spin Resonance Study", *American Journal of Hematology*, vol. 10, pp. 171–179, (1981).

Moore, A. R., et al., "Reduction of Splenic Vascular Resistance During Profusion By Pluronic ® F-68", *Journal of Surgical Research*, vol. 8, pp. 563–566, (1968).

Benner, K. U., et al., "Cold-Induced Platelet Aggregation In Vivo and Its Inhibition By A Nonionic Surface Active Substance", *Thrombosis Research*, vol. 2, pp. 331–342, (1973).

Hymes, A. C., et al., "The Influence of An Industrial Surfactant Pluronic ® F-68, In the Treatment of Hemorrhagic Shock", *Journal of Surgical Research*, vol. 11, pp. 191–197, (1971).

Hoie, J., et al., "Effects of pluronic ® F-68, Poloralkol, On Vascular Resistance In Vivo", *Journal of Surgical Research*, vol. 11, pp. 515–517, (1971).

Grover, F. L., et al., "A Nonionic Surfactant And Blood Viscosity", *Arch. Surg.*, vol. 106, pp. 307–310, (1973).

Grover, F. L., et al., "The Effect of Pluronic ® F-68 On Circulatory Dynamics and Renal And Carotid Artery Flow During Hemorrhagic Shock", *Journal of Surgical Research*, vol. 17, pp. 30–35, (1974).

Ketchum, L. D., et al., "Experimental Use of Pluronic ® F-68 In Microvascular Surgery", *Plastic and Reconstructive Surgery*, vol. 53, pp. 288–292, (1974).

Ketchum, L. D., "Pharmacological alterations in the clotting mechanism: Use in microvascular surgery", *Journal of Hand Surgery*, vol. 3, pp. 407–415, (1978).

Vasco, K. A., et al., "Poloxalkol ® (Pluronic F-68): A priming solution for cardiopulmonary bypass", *Trans. Am. Soc. Artif. Int. Organs*, vol. 18, pp. 526–531, (1972).

(List continued on next page.)

Primary Examiner—John W. Rollins
Attorney, Agent, or Firm—Jones, Askew & Lunsford

[57] ABSTRACT

In accordance with the present invention, a method is provided for treating ischemia resulting from microvascular compromise caused by abnormal cells in the blood stream, which is often a complication of malaria and leukemia. The method is especially useful for treating cerebral malaria. The method comprises administering to an animal or human with the microvascular compromise a therapeutically effective amount of a surface active copolymer with the following general formula:

$$HO(C_2H_4O)_b(C_3H_6O)_a(C_2H_4O)_bH$$

wherein a is an integer such that the hydrophobe represented by $(C_3H_6O)$ has a molecular weight of approximately 950 to 4000 daltons, preferably about 1200 to 3500 daltons, and b is an integer such that the hydrophile portion represented by $(C_2H_4O)$ constitutes approximately 50% to 90% by weight of the copolymer.

21 Claims, No Drawings

Block, N. L., et al., "Acutely traumatized canine ureter, Effects of low molecular weight dextran and surfactant Pluronic F-68", *Urology*, vol. III, pp. 190-194, (1974).

Knize, D. M., et al., "Use of antisludging agents in experimental cold injuries", *Surgery, Gynecology & Obstetrics*, vol. 129, pp. 1019-1026, (1969).

Organ Perfusion and Preservation, (ed. Norman, J. C., Appleton-Century-Crofts, (1968)), Paton, B. C., et al., "The use of a nonionic detergent added to organ perfusates", pp. 105-120.

Smillie, J. A., et al., "Cryopreservation of Human Platelets with Polyvinylpyrrolidone", *Transfusion*, vol. 21, pp. 552-556, (1981).

Gaehtgens, P., et al., "Disaggregation of Human Red Blood Cells by Various Surface-Active Agents as Related to Changes of Cell Shape and Hemolysis", *Act Heamat.*, vol. 33, pp. 82-89, (1975).

Advances in Blood Substitute Research (ed. by Bolin, et al., Alan R. Liss, Inc., New York, (1983)) Sugi, et al., The use of Fluosol-DA (FDA) in emergency situations: a report of 67 clinical sases, Abstract/451.

Lane, T. A., et al., "Reduction in the toxicity of a component of an artifical blood substitute by supercritical fluid fractionation", *Transfusion*, vol. 28, pp. 375-378, (1987).

Lane, T. A., et al., "Paralysis of phagocyte migration due to an artificial blood substitute", *Blood*, vol. 64, pp. 400-405, (1984).

Spiess, B. D., et al., "Protection from cerebral air emboli with perfluorocarbons in rabbits", *Stroke*, vol. 17, pp. 1146-1149, (1986).

Kanter, K. R., et al., "Superiority of perfluorocarbon cardioplegia over blood or crystalloid cardioplegia", *Circulation*, vol. 64, pp. II-75-II-80, (1981).

Harjula, A., et al., "Pefluorocarbon solution as a myocardial preservative", *J. Applied Cardiology*, vol. 2, pp. 121-136, (1987).

Tokioka, M. D., et al., "Effects of intracoronary infusion of arterial blood or Fluosol-DA 20% on regional myocardial metabolism and function during brief coronary artery occlusions", *Laboratory Investigation*, vol. 75, pp. 473-481, (1987).

Benner, K. U., et al., "Über die Wirkung von Pluronic® F-68, einem polyoxypropylene-Poloxyäthylen-Kondensat, auf die ADP-induzierte Thrombocytenaggregation in vitro", *Pflugers Arch.*, vol. 315, pp. 45-52, (1970).

Forman, M. D., et al., "Reduction of infarct size with intracoronary perfluorochemcial in canine preparation of reperfusion", *Circulation*, vol. 71, pp. 1060-1068, (1985).

Forman, M. B., et al., "Beneficial long-term effect on intracoronary perfluorochemcial on infarct size and ventricular function in a canine reperfusion model", *J. Am. Col. of Cardiol.*, pp. 1082-1090, (May, 1987).

Goodman, R. L., et al., "Perfluorocarbon emulsions in cancer therapy: preliminary observation on presently available formulations"*Int. J. Radiation Oncology biol. Phys.*, vol. 10, pp. 1421-1424, (1984).

Technical bulletin entitled "Performance Chemicals".

Technical Bulletin entitled "Pluronic® Block copolymer surfactants".

Perfluorochemical Blood Substitutes, Technical Information Ser. No. 5, Jun. 30, 1978, Revised, Jul. 1, 1981. Manufacturer: The Green Cross Corporation.

Patent Cooperation Treaty International Search Report for PCT Patent Application No. PCT/US87/01067.

Patent Cooperation Treaty International Search Report for the PCT Patent Application No. PCT/US867/01747.

METHOD FOR TREATING VASCULAR OBSTRUCTIONS CAUSED BY ABNORMAL CELLS

CROSS-REFERENCE TO RELATED APPLICATIONS

This is a continuation-in-part of U.S. patent application Ser. No. 522,297 filed on May 11, 1990, now U.S. Pat. No. 5,047,236 which is a continuation of U.S. patent application Ser. No. 07/403,017 filed on Sep. 5, 1989, now abandoned, which is a continuation of U.S. patent application Ser. No. 07/303,791 filed on Jan. 30, 1989, now abandoned, which is a division of U.S. patent application Ser. No. 07/045,459 filed on May 7, 1987, now U.S. Pat. No. 4,801,452, which is a continuation-in-part of U.S. patent application Ser. No. 07/043,888 filed on Apr. 29, 1987, now abandoned, which is a continuation of U.S. patent application Ser. No. 06/863,582 filed on May 15, 1986, now abandoned.

TECHNICAL FIELD

The present invention relates to a method for treating vascular obstructions caused by abnormal cells. More particularly, the present invention is a method for treating vascular obstruction caused by abnormal cells in diseases such as malaria and leukemia.

BACKGROUND OF THE INVENTION

The term "pathological hydrophobic interactions" means detrimental adhesion of components, including, but not limited to, cells and molecules in blood or other biological fluids thereby slowing or stopping the flow of blood or other biological fluid. The term "blood cell" means any cell or cell particle that circulates in the blood including, but not limited to, granulocytes, monocytes, erythrocytes, reticulocytes, platelets, and lymphocytes as well as precursor cells to the aforementioned cells. The term "fibrinolytic enzyme" means any enzyme that is capable of cleaving fibrin or capable of causing fibrin to be cleaved. The terms "isotonic" or "isoosmotic" solution are defined as solutions having the same osmotic pressure as blood. The terms clot, fibrin clot and thrombus are used interchangeably. The term "microcirculation" means blood circulation through blood vessels that are about 50 microns in diameter or less. The term "soluble fibrin" means soluble high molecular weight polymers of fibrinogen and fibrin. The term "biological fluids" means blood, lymph, or other fluids found in animals or humans. The term "ischemic tissue" is any tissue that is damaged from reduced blood flow. The term "anticoagulant" is any compound or agent that inhibits the blood coagulation process. The term "reperfusion injury" means injury to tissue or cells which occurs during reperfusion of damaged tissue with blood. The term "damaged tissue" means tissue damaged by ischemia, burns, toxins or other noxious insult.

It is to be understood that the citation of art contained herein is in no way to be construed as an admission that said art is suitable reference against the present patent application nor should this citation act as a waiver of any rights to overcome said art which may be available to the applicant.

A number of reports have described high amounts of fibrinogen and/or soluble fibrin in the blood of patients with thrombosis, impending thrombosis and many other diseases. These conditions include acute or chronic infection, severe trauma, burns, sickle cell crisis, malaria, leukemia, myocardial infarction, sepsis, shock, and almost any serious illness which produces tissue damage or surgical maneuvers. Evidence indicates that the high concentrations of fibrinogen and/or soluble fibrin may play an important role in the pathology of the conditions. Furthermore, much of the pathology that is encountered in disease may be due to pathological hydrophobic interactions which may be at least partially mediated by high concentration of fibrinogen and/or soluble fibrin.

What is needed is a means of decreasing the adverse effects of soluble fibrin. This would involve blocking the adhesion of soluble fibrin to cells in the circulation thereby blocking the aggregation of such cells and their adhesion or friction to vessel walls in the microvasculature. This would also decrease the risk of thrombosis.

Malaria is a disease caused by parasites of the genus Plasmodium of the class sporozoa in which the asexual cycle (schizogony) takes place in the red blood cells of vertebrates and the sexual cycle (sporogony) in mosquitoes. Members of genus which cause malaria in mammals and birds have closely similar morphology and life cycles. In humans, malaria is caused by four species: *Plasmodium malariae*, *Plasmodium vivax*, *Plasmodium falciparum* and *Plasmodium ovale*. Of these, *Plasmodium falciparum* causes the most severe disease, followed by *Plasmodium vivax*.

People become infected when mosquitoes inject sporozoites in the process of biting. The sporozoites travel to the liver where they develop into cryptozoic schizonts. In time, these are released from the liver as merozoites which infect red blood cells. The asexual merozoites in red blood cells develop through several stages which produce virtually all clinical disease. A portion of them form gametocytes which may be taken up by a mosquito to initiate the sexual stage of development and produce more sporozoites which are available for transmitting the infection to other individuals.

The number of parasites in the peripheral blood varies with the species of malaria. *P. falciparum* is the most serious infection and involves the highest number of infected erythrocytes, at times infecting 10 to 40% of all red blood cells.

The clinical manifestations of malaria are characterized by intermittent febrile paroxysms, secondary anemia and splenic enlargement.[1] It tends to progress from an acute to a chronic state. During the acute stage there are intermittent episodes. During the subsequent chronic stage, periods of latency are broken by a series of relapses similar to the acute primary attack. Malaria caused by *P. falciparum* tends to have few if any relapses, but produces a more severe acute infection with a higher percentage of parasitized erythrocytes.

The incubation period varies from 9 to 40 days for *P. falciparum* malaria, but may be much longer with the other types. Following this period, the patients undergo a prodromal period of a week or more when the number of parasites increases in the blood through the early asexual cycles. During this time, the patients will have no diagnostic clinical manifestations although lassitute, lack of appetite, vague pains in the bones and joints, and daily irregular fevers and chilliness, may be present. The disease may be confused with influenza or similar infections at this time.

The characteristic febrile paroxysms of malaria begin after the prodromal stage. The paroxysms begin with a cold stage or rigor of about an hour during which the patient has a shaking chill, although his temperature may be above normal. A hot stage of longer duration follows, in which the patient has a hot dry skin, flushed face and a temperature of 103° to 106° F., a full rapid pulse, headache, nausea, often vomiting and convulsions in young children. The patient perspires profusely, the temperature falls and the headache disappears so that in a few hours he is exhausted, but symptomless. The febrile paroxysm usually lasts 8 to 12 hours but is longer in *P. falciparum* infections. The paroxysm has been variously attributed to hemolysis from the destruction of red blood cells, shock from the free hemoglobin or metabolic products of the organisms. Virulence is often, but not always, correlated with the intensity of parasitemia. The periodicity of the fevers corresponds with the end of schizogonic cycle when the merozoites with their pigment and debris erupt from red blood cells into the blood stream.

A pernicious form of malaria may be observed in *P. falciparum* infections. Death from acute malaria is confined almost exclusively to this type disease. Victims may develop coma, convulsions and heart failure, with or without high fever. Pernicious infection is characterized by capillary obstruction of adhesive infected red blood cells and cerebral involvement. The cerebral type frequently assumes a comatose form with apathy, stupor and coma. However, it may be meningitic or encephalitic with delirium, psychotic disturbances, paralyses and convulsive seizures. Rapid collapse into coma is due to anoxia, cerebral edema, and increased cerebral pressure. In the septicemic infections, which may simulate a variety of diseases, there may be high fever, headache, delirium, symptoms of sun stroke, cyanosis and hemorrhages in the internal organs. When both the circulatory and nervous systems are involved, the disease may assume a fatal course with rapid loss of strength, cardiac weakness, collapse, and extensive internal hemorrhage.

In the natural course of malaria, the acute symptoms subside, relapses become fewer and latency develops. As a rule, *P. falciparum* infections disappear in less than one year and *P. vivax* infections in about 1½ years although a few may last as long as 5 years or more.

The pathologic changes are primarily vascular. They include the destruction of red blood cells, blockage of the capillaries in the internal viscera and secondarily the anoxic impairment of the liver, brain and other organs. Each successive rupture of merozoites from red blood cells stimulates a humoral and cellular reaction resulting in the phagocytosis of parasitized, infected red blood cells, pigment and cellular debris. In primary *P. vivax* malaria, the red blood cells may show a 10 to 20 percent decrease, but in *P. falciparum* malaria greater destruction may take place. The marked anemia of malaria usually cannot be explained solely on the basis of destruction of infected red blood cells. Tissue anoxia is brought about by the reduction in red blood cells, multiple thrombosis of small blood vessels, and decreased circulating blood volume. The adhesiveness of infected erythrocytes and the changes in blood plasma cause clumping of red blood cells and adherence to the capillary and endothelial cells.

Serious circulatory disturbances, chiefly associated with *P. falciparum* infections, are produced through the blocking of the capillaries by clumped parasitized erythrocytes and phagocytes, increased whole blood and plasma viscosity, and slowing of the capillary circulation. The total plasma proteins, principally serum albumin, are reduced during acute infection, but the euglobulin, fibrinogen and gamma globulin are often increased. The erythrocyte sedimentation rate is increased during acute stages. In fatal *P. falciparum* infections, the brain is edematous, dark red and markedly congested. Microscopically, the cortex is dusty grey or brown and petechial hemorrhages may be visible in perivascular tissues. The cerebral tissues are filled with numerous infected red blood cells, pigmented parasites, pigment and phagocytes. The retarded circulation gives rise to microvascular thrombosis and anoxic necrosis of the perivascular tissues.

Cerebral malaria has certain clinical similarities to cerebral leukemia. In this condition, patients with acute leukemia with very high white blood cell counts which are frequently in excess of 100,000 cells per cubic mm develop signs of acute cerebral ischemia. This may be associated with coagulopathies, circulating soluble fibrin and increased whole blood viscosity in addition to physical rigidity of leukemic cells. If left untreated, this condition may cause death from cerebral ischemia before appropriate therapy for leukemia can be instituted.

What is needed is a therapy to increase blood flow through the brain or other ischemic tissues affected by diseases which cause abnormalities in circulating blood cells such as malaria and leukemia. This would prevent necrosis of tissue during an acute episode and buy time for definitive therapy aimed at the primary disease.

SUMMARY OF THE INVENTION

In accordance with the present invention, a method is provided for treating ischemia resulting from microvascular compromise caused by abnormal cells in the blood stream, which is often a complication of malaria and leukemia. The method comprises administering to an animal or human with the microvascular compromise a therapeutically effective amount of a surface active copolymer with the following general formula:

$$HO(C_2H_4O)_b(C_3H_6O)_a(C_2H_4O)_bH$$

wherein a is an integer such that the hydrophobe represented by $(C_3H_6O)$ has a molecular weight of approximately 950 to 4000 daltons, preferably about 1200 to 3500 daltons, and b is an integer such that the hydrophile portion represented by $(C_2H_4O)$ constitutes approximately 50% to 90% by weight of the copolymer.

The method of the present invention also comprises administering to a human or animal with leukemia, a therapeutically effective amount of a surface active copolymer with the following general formula:

$$HO(C_2H_4O)_b(C_3H_6O)_a(C_2H_4O)_bH$$

wherein a is an integer such that the hydrophobe represented by $(C_3H_6O)$ has a molecular weight of approximately 950 to 4000 daltons, preferably about 1200 to 3500 daltons, and b is an integer such that the hydrophile portion represented by $(C_2H_4O)$ constitutes approximately 50% to 90% by weight of the copolymer.

In addition, the method of the present invention comprises administering to a human or animal with malaria, a therapeutically effective amount of a surface active copolymer with the following general formula:

wherein a is an integer such that the hydrophobe represented by $(C_3H_6O)$ has a molecular weight of approximately 950 to 4000 daltons, preferably about 1200 to 3500 daltons, and b is an integer such that the hydrophile portion represented by (C₂H₄O) constitutes approximately 50% to 90% by weight of the copolymer.

Accordingly, it is an object of the present invention to provide a method for treating disorders with tissue ischemia resulting from microvascular compromise caused by abnormal cells in the blood stream.

It is a further object of the present invention to provide a method for protecting cells during and after an ischemic period.

It is a further object of the present invention to provide a method for treating disorders with acute tissue ischemia resulting from microvascular compromise caused by abnormal cells in the blood stream.

It is a further object of the present invention to provide a method for treating malaria.

It is yet another object of the present invention to provide a method for treating cerebral malaria.

It is yet another object of the present invention to provide a method for treating cerebral leukemia.

These and other objects, features and advantages of the present invention will become apparent after a review of the following detailed description of the disclosed embodiments and the appended claims.

DETAILED DESCRIPTION

Many diseases can cause abnormalities in the circulating blood cells thereby causing blockages in the microcirculation. These blockages in the microcirculation can cause severe ischemia in the tissue which is normally maintained by the microcirculation. Diseases in which this phenomenon can occur include, but are not limited to, malaria and leukemia.

Many of the most severe and life-threatening manifestations of malaria are caused by microvascular occlusion. This is due in part to adhesion of the parasitized red blood cells, probably via specific receptors, to endothelial cells. However, it is also due to adhesion mediated by fibrin, fibrinogen and erythrocyte adhesion and viscosity similar to that involved in other diseases with acute tissue damage. The phenomenon of blood sludging was described as a marked slowing in the microcirculation which could be observed in the sclera of the eyes or other parts of the body with appropriate microscopes.[2,3,4] Such sludging together with increased whole blood viscosity have been observed in malaria in humans[5,6], monkeys[7,8,9], and birds.[10] Knisley, et al., found in Rhesus monkeys with *P. knowlsei* malaria that two visibly separate phenomenon hold red blood cells together. At an early phase of the disease, each red blood cell which contained a parasite developed a change in its outer surface which made the red cells very sticky to other parasitized red cells but not to unparasitized cells. As a result, the parasitized red cells stick tightly together in small clumps. Intravenous heparin prevented development of this stickiness or coating of red cells. This suggests that fibrin was an important mediator. At a later stage of disease, a second larger precipitate was formed between and around both parasitized and unparasitized red cells which bound them together in large masses, each of which had a sticky outer surface. The precipitate was so voluminous that it could be photographed by dark field and could be pulled out in strands by microdisection. Heparin also prevented the formation of this material, suggesting that it too was fibrin. These data on the characteristics of peripheral blood in severe malaria, together with the clinical and pathologic observations, strongly suggest that microvascular occlusion by thrombi and adhesive blood cells is an important contributor to morbidity and mortality with malaria.

Therapy of malaria is directed at reducing or eliminating the infection and to treating symptoms. Patients who develop cerebral or other severe malaria with evidence of acute tissue ischemia may not survive long enough for the anti-malarial drugs to be effective.

The method according to the present invention comprises administering to the animal or human suffering from malaria, and especially cerebral malaria, an effective amount of a surface active copolymer. The surface active copolymer may be administered as a solution by itself or it may be administered with another agent, including but not limited to, a fibrinolytic enzyme, an anticoagulant, or an oxygen radical scavenger.

The surface active copolymer of the present invention comprises the following general formula:

$$HO(C_2H_4O)_b(C_3H_6O)_a(C_2H_4O)_bH$$

wherein a is an integer such that the hydrophobe represented by (C₃H₆O) has a molecular weight of approximately 950 to 4000 daltons, preferably about 1200 to 3500 daltons, and b is an integer such that the hydrophile portion represented by (C₂H₄O) constitutes approximately 50% to 90%, by weight of the copolymer.

The most preferred surface active copolymer for use in the method of the present invention is a copolymer having the following formula:

$$HO(C_2H_4O)_b(C_3H_6O)_a(C_2H_4O)_bH$$

wherein the molecular weight of the hydrophobe (C₃H₆O) is approximately 1750 daltons and the total molecular weight of the compound is approximately 8400 daltons.

The surface active copolymer of the present invention is effective in any condition where there is a pathological hydrophobic interaction between cells and/or molecules. These interactions are believed to be caused by (1) a higher than normal concentration of fibrinogen, (2) generation of intravascular or local soluble fibrin, especially high molecular weight fibrin, (3) increased friction in the microvasculature, or (4) mechanical or chemical trauma to blood components. All of these conditions cause an increase in pathological hydrophobic interactions of blood components such as cells and molecules.

It is believed that fibrin, especially soluble fibrin, increases adhesion of cells to one another, markedly increases friction in small blood vessels and increases viscosity of the blood, especially at low shear rates. The effects of the surface active copolymer of the present invention are believed to be essentially lubrication effects because they reduce the friction caused by the adhesion.

Although not wanting to be bound by the following hypothesis, it is believed that the present invention acts according to the following mechanism: Hydrophobic interactions are crucial determinants of biologic structure. They hold the phospholipids together in membranes and protein molecules in their native configurations. An understanding of the biology of the surface active copolymer is necessary to appreciate the biologic activities of the compound. Water is a strongly hydrogen bonding liquid which, in its fluid state, forms bonds in all directions with surrounding molecules. Exposure of a hydrophobic surface, defined as any surface which forms insufficient bonds with water, produces a surface tension or lack of balance in the hydrogen bonding of water molecules.

This force can be exceedingly strong. The surface tension of pure water is approximately 82 dynes/cm. This translates into a force of several hundred thousand pounds per square inch on the surface molecules.

As two molecules or particles with hydrophobic surfaces approach, they adhere avidly. This adhesion is driven by the reduction in free energy which occurs when water molecules transfer from the stressed non-hydrogen bonding hydrophobic surface to the non-stressed bulk liquid phase.

The energy holding such surfaces together, the work of adhesion, is a direct function of the surface tension of the particles:[11]

$$W_{AB} = \gamma_A + \gamma_B - \gamma_{AB}$$

where $W_{AB}$ = work of adhesion or the energy necessary to separate one square centimeter of particle interface AB into two separate particles, $\gamma_A$ and $\gamma_B$ are the surface tensions of particle A and particle B, $\gamma_{AB}$ the interfacial tension between them.

Consequently, any particles or molecules in the circulation which develop significant surface tensions will adhere to one another spontaneously. Such adhesion within membranes and macromolecules is necessary to maintain their integrity. We use the term "normal hydrophobic interaction" to describe such forces. Under normal circumstances, all cells and molecules in the circulation have hydrophilic non-adhesive surfaces. Receptors and ligands which modulate cell and molecular interactions are generally located on the most hydrophilic exposed surfaces of cells and molecules where they are free to move about in the aqueous media and to interact with one another. Special carrier molecules are necessary to transport lipids and other hydrophobic substances in the circulation. In body fluids such as blood, nonspecific adhesive forces between mobile elements are extremely undesirable. We term these "pathologic hydrophobic interactions" because they restrict movement of normally mobile elements and promote inappropriate adhesion of cells and molecules.

In damaged tissue, hydrophobic, domains normally located on the interior of cells and molecules may become exposed and produce pathologic adhesive surfaces whose interaction compounds the damage. Fibrin deposited along vessel walls also provide an adhesive surface. Such adhesive surfaces appear to be characteristic of damaged tissue. It is believed that the ability of the surface active copolymer to bind to adhesive hydrophobic surfaces and convert them to non-adhesive hydrated surfaces closely resembling those of normal tissues underlies its potential therapeutic activities in diverse disease conditions.

Adhesion due to surface tension described above is different from the adhesion commonly studied in biology. The commonly studied adhesion is due to specific receptor ligand interactions. In particular, it is different from the receptor-mediated adhesion of the fibrinogen - von Willibrand's factor family of proteins.[12]

Both the hydrophilic and hydrophobic chains of the surface active copolymer have unique properties which contribute to biologic activity. The hydrophilic chains of polyoxyethylene are longer than those of most surfactants and they are flexible. They bind water avidly by hydrogen bond acceptor interactions with ether-linked oxygens. These long, strongly hydrated flexible chains are relatively incompressible and form a barrier to hydrophobic surfaces approaching one another. The hydroxyl moieties at the ends of the molecule are the only groups capable of serving as hydrogen bond donors. There are no charged groups.

This extremely limited repertoire of binding capabilities probably explains the inability of the molecule to activate host mediator and inflammatory mechanisms. The POE chains are not necessarily inert, however. Polyoxyethylene can bind cations by ion-dipole interactions with oxygen groups. The crown polyethers and reverse octablock copolymer ionophores are examples of such cation binding.[13] It is possible that the flexible POE chains form configurations which bind and modulate calcium and other cation movements in the vicinity of damaged membranes or other hydrophobic structures.

The hydrophobic component of the surface active copolymer is large, weak and flexible. The energy with which it binds to a cell membrane or protein molecule is less than the energy which holds the membrane phospholipids together or maintains the tertiary conformation of the protein. Consequently, unlike common detergents which dissolve membrane lipids and proteins, the surface active copolymer adheres to damaged spots on membranes and prevents propagation of the injury.

The ability of the surface active copolymer to block adhesion of fibrinogen to hydrophobic surfaces and the subsequent adhesion of platelets and red blood cells is readily demonstrated in vitro. Most surfactants prevent adhesion of hydrophobic particles to one another, however, the surface active copolymer has a unique balance of properties which optimize the anti-adhesive activity while minimizing toxicity. Thus, the surface active copolymer is not routinely used by biochemists who use nonionic surfactants to lyse cells or dissolve membrane proteins. The surface active copolymer protects cells from lysis. The hydrophobe effectively competes with damaged cells and molecules to prevent pathologic hydrophobic interactions, but cannot disrupt the much stronger normal hydrophobic interactions which maintain structural integrity.

The viscosity of blood is generally assumed to be the dominant determinant of flow through vessels with a constant pressure and geometry. In the smallest vessels, however, those in damaged tissue, other factors become significant. When the diameter of the vessel is less than that of the cell, the blood cell must deform in order to enter the vessel and then must slide along the vessel wall producing friction. The deformability of blood cells entering small vessels has been extensively studied,[14,15] but the adhesive or frictional component has not. The adhesion of cells to vessel walls is generally attributed to specific interactions with von Willebrand's factor and other specific adhesive molecules.[16] Our data suggests that in pathologic situations, friction resulting from nonspecific physicochemical adhesion between the cell and the vessel wall becomes a major determinant of flow.

Mathematically, both the strength of adhesion between two particles and the friction force which resists sliding of one along the other are direct functions of their surface tensions which are largely determined by their degree of hydrophobic interaction. The friction of a cell sliding through a small vessel consists of an adhesion component and a deformation component which are in practice difficult to separate:[17]

$$F = Fa + Fd$$

where F is the friction of cells, Fa is the adhesion component, and Fd is the deformation component.

The deformation component within a vessel differs from that required for entry into the vessel. It may be similar to that which occurs in larger vessels with blood flowing at a high rate of shear.[18] Friction within blood vessels has been studied very little, but undoubtedly involves the same principles which apply to polymer systems in which the friction force correlates directly with the work of adhesion.[19]

$$Fa = k\ WA + c$$

where Fa is the adhesional component of the friction force, WA the work of adhesion, and k and c constants which pertain to the particular system studied. Many lubricants act as thin films which separate the two surfaces and reduce adhesion.[20]

The effects of the surface active copolymer on microvascular blood flow were evaluated in several models ranging from artificial in vitro systems where critical variables could be rigidly controlled to in vivo systems mimicking human disease. First, the surface active copolymer can be an effective lubricant when used at therapeutic concentrations in a model designed to simulate movement of large cells through small vessels. It markedly reduced the adhesive component of friction, but had no detectable effect on the deformation component of friction. Second, the surface active copolymer greatly accelerates the flow through the narrow channels formed by the thrombogenic surfaces of glass and air. A drop of blood was placed on a cover slip and viewed under a microscope with cinemicroscopy during the time it took the blood to flow to the edges of the cover slip in response to gentle pressure. The surface active copolymer inhibited the adhesion of platelets to the glass and maintained the flexibility of red cells which enabled them to pass through the microscopic channels. While the surface active copolymer did not inhibit the formation of rouleaux by red cells, it did cause the rouleaux to be more flexible and more easily disrupted. Third, the surface active copolymer increases the flow of blood through tortuous capillary-sized fibrin-lined channels by over 20-fold. It decreased viscosity of the blood by an amount (10%) far too small to account for the increased flow.

In a more physiologic model, the surface active copolymer increased coronary blood flow by a similar amount in isolated rat hearts perfused with human red blood cells at a 30% hematocrit following ischemic damage.

In an in vivo model of stroke produced by ligature of the middle cerebral artery of rabbits, the surface active copolymer increases blood flow to ischemic brain tissue. As much as a two-fold increase was measured by a hydrogen washout technique. In each of these models, there were controls for hemodilution and there was no measurable effect on viscosity at any shear rate measured.

It is believed that available data suggests that the surface active copolymer acts as a lubricant to increase blood flow through damaged tissues. It blocks adhesion of hydrophobic surfaces to one another and thereby reduces friction and increases flow. This hypothesis is strengthened by the observation that the surface active copolymer has little effect on blood flow in normal tissues where such frictional forces are small.[21]

The surface active copolymers of the present invention are not metabolized by the body and are quickly eliminated from the blood. The half-life of the copolymer in the blood is believed to be approximately two hours. It is to be understood that the surface active copolymer in the improved fibrinolytic composition of the present invention is not covalently bound to any of the other components in the composition nor is it covalently bound to any proteins.

The surface active copolymer has little effect on the viscosity of normal blood at shear rates ranging from 2.3 sec$^{-1}$ (low) to 90 sec$^{-1}$ (high). However, it markedly reduces the abnormally high viscosity found in postoperative patients and in those with certain pathologic conditions. This observation posed two questions: 1) what caused the elevated whole blood viscosity in these patients and, 2) by what mechanism did the surface active copolymer, which has only minor effects on the blood viscosity of healthy persons, normalize pathologic elevations in viscosity?

It is generally accepted that hematocrit and plasma fibrinogen levels are the major determinants of whole blood viscosity. This has been confirmed in normal individuals and in many patients with inflammatory conditions. However, these factors could not explain the changes that were observed. In patients having coronary artery cardiac bypass surgery, it was found that hematocrit fell an average of 23±4% and fibrinogen fell 48±9% within six hours after surgery. The viscosity did not decrease as expected, but increased from a mean of 23±2 to 38±4 centipoise (at a shear rate of 2.3 sec$^{-1}$). Viscosities in excess of 100 were found in some patients. The abnormally high viscosity of blood was associated with circulating high molecular weight polymers of soluble fibrin.[22] The soluble fibrin levels rose from 19±5 µg/ml to 43±6 µg/ml during surgery. These studies utilized a colorimetric enzymatic assay for soluble fibrin[23] and Western blotting procedures with SDS agarose gels to determine the molecular weight of the large protein polymers.[24]

In the absence of specific receptors, cells and molecules in the circulation adhere to one another if the adherence reduces the free energy or surface tension between them. An assessment of the surface tension of various components of the blood can be made by measuring contact angles.

Red blood cells, lymphocytes, platelets, and neutrophils all have contact angles in the range of 14 to 17 degrees. Peripheral blood proteins, such as albumin, $\alpha_2$macroglobulin, and Hageman factor have contact angles in the slightly lower range of 12 to 15 degrees. This means that these proteins have no adhesive energy for the cells. In contrast, fibrinogen has a contact angle of 24 degrees and soluble fibrin of 31 degrees. Consequently, fibrinogen adheres weakly to red blood cells and other cells in the circulation promoting rouleaux formation. Fibrin promotes a very much stronger adhesion than fibrinogen because its elevated contact angle and its tendency to form polymers with fibrinogen. Soluble fibrin in the circulation produces the increased adhesion which results in a very markedly increased viscosity at low shear rates. This adhesion also involves the endothelial walls of the blood vessels. If the adhesive forces are insufficient to slow movement of cells, they produce an increased friction. This is especially important in the very small blood vessels and capillaries whose diameters are equal to or less than that of the circulating cells. The friction of cells sliding through these small vessels is significant. The surface active copolymer of the present invention blocks the adhesion of fibrinogen and fibrin to hydrophobic surfaces of cells and endothelial cells. This prevents their adhesion and lubricates them so there is a greatly reduced resistance to flow. This can be measured only partially by measurements of viscosity.

Whether a certain fibrinogen level is sufficient to cause a problem in circulation is dependent upon several parameters of the individual patient. High hematocrits and high levels of fibrinogen are widely regarded as the primary contributors to increased viscosity. However, elevated fibrinogen levels are frequently associated with elevated soluble fibrin in the circulation. Careful studies have demonstrated that the fibrin is frequently responsible for the most severe changes. The normal level of fibrinogen is 200–400 $\mu$g/ml. It has been determined that, in most patients, fibrinogen levels of greater than approximately 800 $\mu$g/ml will cause the high blood viscosity at the low shear rates mentioned hereinabove. The normal level of soluble fibrin has been reported to be approximately 9.2±1.9.[25] Using the Wiman and Rånby assay, viscosity at low shear rates was unacceptably high above about 15 $\mu$g/ml. It must be understood that soluble fibrin means molecular species that have a molecular weight of from about 600,000 to several million.

Numerous methods have been used for demonstrating soluble fibrin. These include cryoprecipitation, especially cryofibrinogen. Heparin has been used to augment the precipitate formation. Ethanol and protamine also precipitate fibrin from plasma. Modern techniques have demonstrated that the soluble fibrin in the circulation is generally complexed with solubilizing agents. These are most frequently fibrinogen or fibrin degradation products. Des AA fibrin, in which only the fibrin of peptide A moieties have been cleaved, tends to form relatively small aggregates consisting of one molecule of fibrin with two of fibrinogen. If both the A and B peptides have been cleaved to produce des AABB fibrin, then much larger aggregates are produced in the circulation. Fibrin degradation products can polymerize with fibrin to produce varying size aggregates depending upon the particular product involved.

Soluble fibrin in the circulation can markedly increase blood viscosity, especially at low shear rates. However, the relevance of this for clinical situations remains unclear. Viscosity assesses primarily the aggregation of red blood cells which is only one of many factors which determine in vivo circulation. Other factors affected by soluble fibrin are the endothelial cells, white blood cells and platelets. Soluble fibrin is chemotactic for endothelial cells, adheres to them avidly and causes their disorganization. It also has stimulatory effects for white blood cells, especially macrophages. Some of the effects of soluble fibrin may be mediated by specific receptors on various types of cells. However, since the free energy, as measured by contact angles of soluble fibrin, is less than that of any other plasma protein, it adheres avidly by a nonspecific hydrophobic interactions to virtually all formed elements in the blood.

Circulating soluble fibrin is normally cleared by macrophages and fibrinolytic mechanisms without producing damage. However, if the production of soluble fibrin is too great or if the clearance mechanisms have been compromised or if complicating disease factors are present, then soluble fibrin can induce deleterious reactions.

Soluble fibrin is produced in damaged or inflamed tissues. Consequently, its effects are most pronounced in these tissues where it coats endothelial cells and circulating blood cells in a fashion which markedly reduces perfusion. The largest effects are in the small blood vessels where soluble fibrin coating the endothelial cells and white blood cells produces a severe increase in friction to the movement of white cells through the small vessels. Friction appears to be a much more severe problem with white blood cells and red blood cells because they are larger and much more rigid.

If production of soluble fibrin is sufficient, then effects are noticed in other areas. The best studied is the adult respiratory distress syndrome where soluble fibrin produced in areas of damaged tissue produces microthrombi and other processes in the lungs which can cause pulmonary failure. However, lesser degrees of vascular compromise can be demonstrated in many other organs.

Soluble fibrin, either alone or in complex with fibrinogen and other materials, is now recognized as being a major contributor to the pathogenesis of a diverse range of vascular diseases ranging from coronary thrombosis through trauma, burns, reperfusion injury following transplantation, or any other condition where there has been localized or generalized activation of coagulation. A recent study demonstrated that virtually all patients with acute myocardial infarction or unstable angina pectoris have markedly elevated levels of soluble fibrin in their circulation.

An example of the effects of soluble fibrin has been shown in the studies using dogs. A normal dog is subjected to a hysterectomy. Then, while the animal is still under anesthesia, the external jugular vein is carefully dissected. Alternatively, the vein may be occluded by gentle pressure with the fingers for seven minutes. It is examined by scanning electron microscopy for adhesion of fibrin, red blood cells and other formed elements.

One finds that very few cells adhere to the endothelia of veins from dogs which had not undergone hysterectomy, whether or not there had been stasis produced by seven minutes occlusion. Similarly, there was only a small increase in adhesion of red blood cells to the endothelium of the jugular vein in animals who had undergone hysterectomy. If, however, the animals had a hysterectomy in addition to mild seven minute occlusion of the veins, then there was a striking increase in adhesion of formed elements of blood to the endothelial surfaces in some cases producing frank mural thrombi. Both red blood cells and fibrin were visibly adherent to the endothelial surfaces. In addition, there was disruption of the normal endothelial architecture. All of the animals had elevated levels of soluble fibrin after the surgery. This model demonstrates the effects of soluble fibrin produced by relatively localized surgery to produce a greatly increased risk of deep vein thrombosis at a distant site.

The surface active copolymer of the present invention addresses the problems of fibrin and fibrinogen in the blood by inhibiting the adhesion of fibrin, fibrinogen, platelets, red blood cells and other detectable elements of the blood stream. It blocks the formation of a thrombus on a surface. The surface active copolymer of the present invention has no effect on the viscosity of water or plasma. However, it markedly increases the rate of flow of water and plasma in small segments through tubes. The presence of air interfaces at the end of the columns or air bubbles which provide a significant surface tension produce a friction along the walls of the tubes. The surface active copolymer of the present invention reduces this surface tension and the friction and improves flow. This is an example whereby the surface active copolymer of the present invention improves flow of fluid through tissues through a tube even though it has no effect on the viscosity of the fluid as usually measured.

The surface active copolymer of the present invention has only a small effect on the viscosity of whole blood from normal individuals. It has little effect on the increase that occurs with high hematocrit. However, it has an effect on the very large increase in viscosity at low shear rates thought to be caused by soluble fibrin and fibrinogen polymers.

Recent studies demonstrate that the surface active copolymer also has the ability to protect myocardial and other cells from a variety of noxious insults. During prolonged ischemia, myocardial cells undergo "irreversible injury." Cells which sustain irreversible injury are morphologically intact but are unable to survive when returned to a normal environment. Within minutes of reperfusion with oxygenated blood, cells containing such occult lesions develop swelling and contraction bands and die.

Irreversibly injured myocardial cells have mechanical and osmotic fragility and latent activation of lipases, proteases and other enzymes. Reperfusion initiates a series of events including calcium loading, cell swelling, mechanical membrane rupture and the formation of oxygen free radicals which rapidly destroy the cell. The surface active copolymer retards such injury in the isolated perfused rat heart model. The mechanisms probably include osmotic stabilization and increased mechanical resistance in a fashion similar to that known for red blood cells.

The protective effects of the surface active copolymer on the myocardium are not limited to the myocardial cells. It also protects the endothelial cells of the microvasculature as assessed morphologically. By maintaining the integrity of such cells and helping to restore and maintain non-adhesive surfaces, the surface active copolymer tends to reduce the adhesion of macromolecules and cells in the microvasculature, to reduce coronary vascular resistance and to retard development of the no reflow phenomenon.

Examples of conditions where the present invention can be used is in the treatment of sickle cell disease and preservation of organs for transplantation. In both of these embodiments, blood flow is reduced because of pathologic hydrophobic interactions.

The method for treating malaria and leukemia of the present invention includes administering the solution of surface active copolymer by intravenous injection. However, it is to be understood that the solution of surface active copolymer can be administered by intramuscular, subcutaneous, parenteral, or any other route of injection. It is contemplated as part of the present invention that the surface active copolymer could be administered orally either with an agent that promotes absorption of the copolymer by the gastrointestinal tract or by the surface active copolymer itself. In addition, the surface active copolymer can be administered transdermally.

The final concentration of surface active copolymer in blood or other biologic fluids used to practice the present invention is between approximately 0.01 and 10 mg/ml. The preferred concentration of surface active copolymer used to practice the present invention is between approximately 0.1 and 2 mg/ml with the most preferred concentration between approximately 0.4 and 0.8 mg/ml of fluid.

Solutions which may be employed in the preparation of the copolymer solution, include, but are not limited to, saline (a solution of sodium chloride, containing approximately 8.5 to 9.5 grams of sodium chloride in 1000 cc of purified water), Ringer's solution, lactated Ringer's solution, Krebs-Ringer's solution, and various sugar solutions. All of these solutions are well known to one of ordinary skill in the art. However, it is to be understood that the copolymer solution of the present invention may be administered as a solution that is not isotonic.

The present invention includes use of the surface active copolymer with an effective amount of anticoagulant to permit blood flow through ischemic tissue that occurs during severe malaria or leukemia. Anticoagulants that can be used with the present invention include, but are not limited to, heparin, low molecular weight heparin, coumarin derivatives, and warfarin. It is to be understood that the surface active copolymer of the present invention could be used with any one anticoagulant or with a combination of anticoagulants. It is also understood that the concentration of anticoagulant to be used with the surface active copolymer is well known to those of ordinary skill in the art. It has been found that administration of the surface active copolymer with anticoagulants increases blood flow through the ischemic tissue in a synergistic manner.

The surface active copolymer is preferably an ethylene oxide-propylene oxide condensation product with the following general formula:

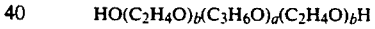

$$HO(C_2H_4O)_b(C_3H_6O)_a(C_2H_4O)_bH$$

wherein a is an integer such that the hydrophobe represented by $(C_3H_6O)$ has a molecular weight of approximately 950 to 4000 daltons, preferably from 1750 to 3500 daltons, and b is an integer such that the hydrophile portion represented by $(C_2H_4O)$ constitutes from about 50% to 90% by weight of the compound. These copolymers are sold under the general trademark of Pluronic ® polyols and are available from the BASF Corporation (Parsippany, N.J.).

The copolymer can be used over a wide range of concentrations with no severe adverse side effects. It is believed that the copolymer is rapidly excreted intact; as much as 90% of the copolymer administered is excreted within three hours. Because of its low toxicity and the rapid clearance from the body, the copolymer can be administered over a long period of time.

The surface active copolymer of the present invention may be employed by admixing with blood in any standard manner. Preferably, however, the solutions are intravenously injected into the blood stream either as a bolus, slow drip or a combination of both. The solutions are generally admixed with the blood in a manner so as to maintain a substantially steady venous pressure.

A bolus injection of the copolymer solution can be administered intravenously. For example, a 10% to 20% solution of the copolymer in half normal saline is injected within a two minute period so that the blood concentration of copolymer is approximately 0.6 mg/ml. In addition, it can be advantageous to administer a solution of the copolymer by intravenous drip at a rate of about 25 mg/kg body weight/hour to obtain a blood concentration of the copolymer of approximately 0.6 mg/ml for up to four days or longer.

The surface active copolymer blocks are formed by condensation of ethylene oxide and propylene oxide at elevated temperature and pressure in the presence of a basic catalyst. There is some statistical variation in the number of monomer units which combine to form a polymer chain in each copolymer. The molecular weights given are approximations of the average weight of copolymer molecule in each preparation. It is to be understood that the blocks of propylene oxide and ethylene oxide do not have to be pure. Small amounts of other materials can be admixed so long as the overall physical chemical properties are not substantially changed. A more detailed discussion of the preparation of these products is found in U.S. Pat. No. 2,674,619, which is incorporated herein by reference.

Illustrative ethylene oxide-propylene oxide condensation products which may be employed in the preparation of the fibrinolytic composition of the present invention include, but are not limited to, the following copolymers:

1. A polyol with an average molecular weight of 4700 daltons containing approximately 80% by weight ethylene oxide.
2. A polyol with an average molecular weight of 3400 daltons containing approximately 50% by weight ethylene oxide.
3. A polyol with an average molecular weight of 7700 daltons containing approximately 70% by weight ethylene oxide.
4. A polyol with an average molecular weight of 14,600 daltons containing approximately 80% by weight ethylene oxide.
5. A polyol with an average molecular weight of 12,600 daltons containing approximately 70% by weight ethylene oxide.
6. A polyol with an average molecular weight of 9500 daltons containing approximately 90% by weight ethylene oxide.

The preferred ethylene oxide-propylene oxide copolymer for use in the fibrinolytic composition of the present invention is a copolymer having the following formula:

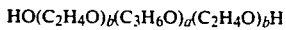

wherein the molecular weight of the hydrophobe ($C_3H_6O$) is approximately 1750 daltons and the total molecular weight of the compound is approximately 8400 daltons.

This invention is further illustrated by the following example, which is not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

A traveller returns to the U.S. after a trip to Africa. In a period of weeks he develops an influenza like infection which becomes progressively severe. He develops neurologic symptoms with apathy stupor and impending coma. Peripheral blood demonstrates a large proportion of the red cells to be infected with *P. falciparum*. The patient is treated immediately with a 50 (mg/kg) bolus of a surface active copolymer with following general formula:

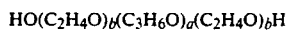

wherein the molecular weight of the hydrophobe ($C_3H_6O$) is approximately 1750 daltons and the total molecular weight of the compound is approximately 8400 daltons.

This bolus administration was followed by a continuous infusion of 25 mg/kg per hour for 3 days. He is immediately started on chloroquine and other antimalarial drugs. The mental condition improves within hours. There is no evidence of further deterioration of renal, hepatic, or other organ function. The patient recovers progressively and completely from the infection.

It should be understood, of course, that the foregoing relates only to a preferred embodiment of the present invention and that numerous modifications or alterations may be made therein without departing from the spirit and the scope of the invention as set forth in the appended claims.

[1] Brown, H. W. Blood tissue protoza of man. Basic Clinical Parasitology. Third Edition. Meredith Corporation. Chapter 4;45-98, 1969.
[2] Knisely, M. H. Intravascular erythrocyte aggregation (blood sludge). Handbook of Physiology. Philip Dow, Editor. American Physiological Society. Chapter 63:2249-2292, 1965
[3] Bloch, E. H. Microscopic observations of the circulating blood in the bulbar conjunctiva in man in health and disease. Ergb. Anat. Entwicklungsgesch. 35:1, 1956.
[4] Knisely, M. H., Bloch, E. H., Eliot, T. S. and Warner, L. Sludged blood. Science 106:431, 1947
[5] See footnote 2
[6] See footnote 2
[7] Knisely, M. H., Stratman-Thomas, W. K. and Eliot, T. S. Capillary circulation in the malaria infected monkey. A cinematographic study. J. Am. Med. Assoc. 116:2430, 1941
[8] Knisely, M. H., Stratman-Thomas, W. K., Eliot, T. S. and Bloch, E. H. Knowlesi malaria in monkeys. I. Microscopic pathological circulatory physiology of rhesus monkeys during acute knowlesi malaria. J. Nat. Malaria. Soc. 4:285, 1945
[9] Knisely, M. H., Stratman-Thomas, W. K., Eliot, T. S. and Bloch, E. H. Knowlesi malaria in monkeys. II. A first step in separation of mechanical pathologic circulatory factors on one sludge disease from possible specific toxic factors of that disease. Am. J. Physiol. 159:575, 1949
[10] Lack, A. R. The occurrence of intravascular agglutination in avian malaria. *Science* 96:520, 1942
[11] Adamson A. W. *Physical Chemistry of Surfaces*. Fourth Edition, John Wiley & Sons, New York, 1982
[12] See generally *Hemostasis and Thrombosis. Basic Principles and Clinical Practice*, ed. by Colman, et al., J. B. Lippincott Company (1987)
[13] Atkinson, T. P., et al., Ion transport mediated by copolymers composed of polyoxyethylene and polyoxypropylene. *Am J Physiol* 254;C20, 1988
[14] Brooks D. E. and Evans E. A. Rheology of blood cells, in *Clinical Hemorheology. Applications in Cardiovascular and Hematological Disease, Diabetes, Surgery and Gynecology*
[15] S. Chien, J. Dormandy, E. Ernst, and A. Matrai, eds, Martinus Nijhoff Publishers, Dordrecht, 1987
[16] Thompson A. R. and Harker L. A. *Manual of Hemostasis and Thrombosis*, Edition 3, F. A. Davis Company, Philadelphia, 1983
[17] Lee L. H. Effect of surface energetics on polymer friction and wear, in *Advances in Polymer Friction and Wear*, Polymer Science and Technology, volume 5A. L.H. Lee, editor, Plenum Press, New York, 1974
[18] See footnote 13
[19] See footnote 16
[20] See footnote 17
[21] Grover F. L., Kahn R. S., Heron M. W., and Paton B. C., A nonionic surfactant and blood viscosity. *Arch Surg* 106:307, 1973
[22] Papadea C. and Hunter R. Effect of RheothRx ™ copolymer on blood viscosity related to fibrin(ogen) concentration. *FASEB J* 2:A384, 1988
[23] Wiman, B. and Rånby, M., Determination of soluble fibrin in plasma by a rapid and quantitative spectrophotometric assay. *Thromb. Haemost* 55:189, 1986
[24] Connaghan D. G., Francis C. W., Lane D. A., and Marder V. J. Specific identification of fibrin polymers, fibrinogen degradation products, and crosslinked fibrin degradation products in plasma and serum with a new sensitive technique. *Blood* 65:589. 1985
[25] See footnote 22.

I claim:

1. A method for treating vascular obstructions caused by abnormal cells in a human or animal comprising the step of injecting into the human or animal with the vascular obstructions a solution with an effective concentration of a surface active copolymer with the following general formula:

$$HO(C_2H_4O)_b(C_3H_6O)_a(C_2H_4O)_bH$$

wherein a is an integer such that the hydrophobe represented by ($C_3H_6O$) has a molecular weight of between approximately 950 to 4000 daltons, and b is an integer such that the hydrophile portion represented by ($C_2H_4O$) constitutes between approximately 50% to 90% by weight of the copolymer.

2. The method of claim 1, wherein the surface active copolymer has the following formula:

$$HO(C_2H_4O)_b(C_3H_6O)_a(C_2H_4O)_bH$$

wherein a is an integer such that the hydrophobe represented by ($C_3H_6O$) has a molecular weight of between approximately 1200 to 3500 daltons, and b is an integer such that the hydrophile portion represented by ($C_2H_4O$) constitutes between approximately 50% to 90% by weight of the copolymer.

3. The method of claim 1, wherein the surface active copolymer has the following formula:

$$HO(C_2H_4O)_b(C_3H_6O)_a(C_2H_4O)_bH$$

wherein the molecular weight of the hydrophobe ($C_3H_6O$) is approximately 1750 daltons and the total molecular weight of the compound is approximately 8400 daltons.

4. A method for treating vascular obstructions caused by abnormal cells in a human or animal comprising the step of injecting intravenously into the human or animal with the vascular obstructions a solution with an effective concentration of a surface active copolymer with the following general formula:

$$HO(C_2H_4O)_b(C_3H_6O)_a(C_2H_4O)_bH$$

wherein a is an integer such that the hydrophobe represented by ($C_3H_6O$) has a molecular weight of between approximately 950 to 4000 daltons, and b is an integer such that the hydrophile portion represented by ($C_2H_4O$) constitutes between approximately 50% to 90% by weight of the copolymer.

5. The method of claim 4, wherein the surface active copolymer has the following formula:

$$HO(C_2H_4O)_b(C_3H_6O)_a(C_2H_4O)_bH$$

wherein a is an integer such that the hydrophobe represented by ($C_3H_6O$) has a molecular weight of between approximately 1200 to 3500 daltons, and b is an integer such that the hydrophile portion represented by ($C_2H_4O$) constitutes between approximately 50% to 90% by weight of the copolymer.

6. The method of claim 4, wherein the surface active copolymer has the following formula:

$$HO(C_2H_4O)_b(C_3H_6O)_a(C_2H_4O)_bH$$

wherein the molecular weight of the hydrophobe ($C_3H_6O$) is approximately 1750 daltons and the total molecular weight of the compound is approximately 8400 daltons.

7. A method for treating vascular obstructions caused by abnormal cells in a human or animal comprising the step of injecting intramuscularly into the human or animal with the vascular obstructions a solution with an effective concentration of a surface active copolymer with the following formula:

$$HO(C_2H_4O)_b(C_3H_6O)_a(C_2H_4O)_bH$$

wherein a is an integer such that the hydrophobe represented by ($C_3H_6O$) has a molecular weight of between approximately 950 to 4000 daltons, and b is an integer such that the hydrophile portion represented by ($C_2H_4O$) constitutes between approximately 50% to 90% by weight of the copolymer.

8. The method of claim 7, wherein the surface active copolymer has the following formula:

$$HO(C_2H_4O)_b(C_3H_6O)_a(C_2H_4O)_bH$$

wherein a is an integer such that the hydrophobe represented by ($C_3H_6O$) has a molecular weight of between approximately 1200 to 3500 daltons, and b is an integer such that the hydrophile portion represented by ($C_2H_4O$) constitutes between approximately 50% to 90% by weight of the copolymer.

9. The method of claim 7, wherein the surface active copolymer has the following formula:

$$HO(C_2H_4O)_b(C_3H_6O)_a(C_2H_4O)_bH$$

wherein the molecular weight of the hydrophobe ($C_3H_6O$) is approximately 1750 daltons and the total molecular weight of the compound is approximately 8400 daltons.

10. A method for treating malaria in a human or animal comprising the step of injecting into the human or animal with malaria a solution with an effective concentration of a surface active copolymer with the following general formula:

$$HO(C_2H_4O)_b(C_3H_6O)_a(C_2H_4O)_bH$$

wherein a is an integer such that the hydrophobe represented by ($C_3H_6O$) has a molecular weight of between approximately 950 to 4000 daltons, and b is an integer such that the hydrophile portion represented by ($C_2H_4O$) constitutes between approximately 50% to 90% by weight of the copolymer.

11. The method of claim 10, wherein the surface active copolymer has the following formula:

$$HO(C_2H_4O)_b(C_3H_6O)_a(C_2H_4O)_bH$$

wherein a is an integer such that the hydrophobe represented by ($C_3H_6O$) has a molecular weight of between approximately 1200 to 3500 daltons, and b is an integer such that the hydrophile portion represented by ($C_2H_4O$) constitutes between approximately 50% to 90% by weight of the copolymer.

12. The method of claim 10, wherein the surface active copolymer has the following formula:

$$HO(C_2H_4O)_b(C_3H_6O)_a(C_2H_4O)_bH$$

wherein the molecular weight of the hydrophobe ($C_3H_6O$) is approximately 1750 daltons and the total molecular weight of the compound is approximately 8400 daltons.

13. The method of claim 10, wherein the malaria is cerebral malaria.

14. A method for treating malaria in a human or animal comprising the step of injecting intravenously into the human or animal with malaria a solution with an effective concentration of a surface active copolymer with the following general formula:

$$HO(C_2H_4O)_b(C_3H_6O)_a(C_2H_4O)_bH$$

wherein a is an integer such that the hydrophobe represented by ($C_3H_6O$) has a molecular weight of between approximately 950 to 4000 daltons, and b is an integer such that the hydrophile portion represented by ($C_2H_4O$) constitutes between approximately 50% to 90% by weight of the copolymer.

15. The method of claim 14, wherein the surface active copolymer has the following formula:

$$HO(C_2H_4O)_b(C_3H_6O)_a(C_2H_4O)_bH$$

wherein a is an integer such that the hydrophobe represented by ($C_3H_6O$) has a molecular weight of between approximately 1200 to 3500 daltons, and b is an integer such that the hydrophile portion represented by ($C_2H_4O$) constitutes between approximately 50% to 90% by weight of the copolymer.

16. The method of claim 14, wherein the surface active copolymer has the following formula:

$$HO(C_2H_4O)_b(C_3H_6O)_a(C_2H_4O)_bH$$

wherein the molecular weight of the hydrophobe ($C_3H_6O$) is approximately 1750 daltons and the total molecular weight of the compound is approximately 8400 daltons.

17. The method of claim 14, wherein the malaria is cerebral malaria.

18. A method for treating malaria in a human or animal comprising the step of injecting intramuscularly into the human or animal with malaria a solution with an effective concentration of a surface active copolymer with the following formula:

$$HO(C_2H_4O)_b(C_3H_6O)_a(C_2H_4O)_bH$$

wherein a is an integer such that the hydrophobe represented by ($C_3H_6O$) has a molecular weight of between approximately 950 to 4000 daltons, and b is an integer such that the hydrophile portion represented by ($C_2H_4O$) constitutes between approximately 50% to 90% by weight of the copolymer.

19. The method of claim 18, wherein the surface active copolymer has the following formula:

$$HO(C_2H_4O)_b(C_3H_6O)_a(C_2H_4O)_bH$$

wherein a is an integer such that the hydrophobe represented by ($C_3H_6O$) has a molecular weight of between approximately 1200 to 3500 daltons, and b is an integer such that the hydrophile portion represented by ($C_2H_4O$) constitutes between approximately 50% to 90% by weight of the copolymer.

20. The method of claim 18, wherein the surface active copolymer has the following formula:

$$HO(C_2H_4O)_b(C_3H_6O)_a(C_2H_4O)_bH$$

wherein the molecular weight of the hydrophobe ($C_3H_6O$) is approximately 1750 daltons and the total molecular weight of the compound is approximately 8400 daltons.

21. The method of claim 18, wherein the malaria is cerebral malaria.

* * * * *